(12) United States Patent
Frey et al.

(10) Patent No.: US 8,100,828 B2
(45) Date of Patent: Jan. 24, 2012

(54) DISTRACTION AND RETRACTION SYSTEM FOR SPINAL SURGERY

(75) Inventors: George Frey, Englewood, CO (US); John L. White, Bartlett, TN (US); Steven D. DeRidder, Bartlett, TN (US)

(73) Assignee: George Frey, Englewood, CO (US)

( * ) Notice: Subject to any disclaimer, the term of this patent is extended or adjusted under 35 U.S.C. 154(b) by 675 days.

(21) Appl. No.: 10/720,656

(22) Filed: Nov. 24, 2003

(65) Prior Publication Data

US 2004/0230191 A1 Nov. 18, 2004

Related U.S. Application Data

(60) Provisional application No. 60/428,800, filed on Nov. 23, 2002.

(51) Int. Cl.
*A61B 17/02* (2006.01)
(52) U.S. Cl. ........................................................ 600/234
(58) Field of Classification Search ................ 66/57, 56, 66/87, 90; 600/231; 623/232, 234, 235, 623/231
See application file for complete search history.

(56) References Cited

U.S. PATENT DOCUMENTS

| | | | |
|---|---|---|---|
| 563,236 A | 6/1896 | Penhall | |
| 1,157,202 A * | 10/1915 | Bates | 600/208 |
| 1,400,616 A * | 12/1921 | McCrory et al. | 600/217 |
| 1,839,726 A * | 1/1932 | Arnold | 600/233 |
| 2,473,266 A * | 6/1949 | Wexler | 600/215 |
| 2,623,517 A * | 12/1952 | Barlow et al. | 600/233 |
| 2,661,735 A | 12/1953 | Darden | |
| 3,054,398 A | 9/1962 | Kobler | |
| 3,752,149 A | 8/1973 | Ungar et al. | |
| 3,788,318 A | 1/1974 | Kim et al. | |
| 3,965,890 A * | 6/1976 | Gauthier | 600/215 |
| 4,263,899 A | 4/1981 | Burgin | |
| 4,545,374 A | 10/1985 | Jacobson | |
| 4,616,635 A | 10/1986 | Caspar et al. | |
| 4,716,901 A | 1/1988 | Jackson et al. | |
| 4,747,394 A | 5/1988 | Watanabe | |
| 4,747,395 A | 5/1988 | Brief | |
| 4,765,311 A | 8/1988 | Kulik et al. | |
| 4,817,587 A | 4/1989 | Janese | |
| 4,852,552 A | 8/1989 | Chaux | |
| 4,899,729 A | 2/1990 | Gill et al. | |
| 5,027,793 A | 7/1991 | Engelhardt et al. | |
| 5,052,373 A | 10/1991 | Michelson | |
| 5,125,396 A | 6/1992 | Ray | |
| 5,139,511 A | 8/1992 | Gill et al. | |
| 5,158,545 A | 10/1992 | Trudell et al. | |
| 5,163,949 A | 11/1992 | Bonutti | |
| 5,197,971 A | 3/1993 | Bonutti | |
| 5,312,417 A | 5/1994 | Wilk | |
| 5,339,803 A | 8/1994 | Mayzels et al. | |

(Continued)

FOREIGN PATENT DOCUMENTS

DE 87 04 901 U 7/1987

(Continued)

*Primary Examiner* — David Isabella
*Assistant Examiner* — Ann Schillinger

(57) ABSTRACT

The surgical instrumentation system is adapted to provide an operative approach to the spinal column and maintain distraction of adjacent vertebrae. The system includes at least one retractor and a pair of opposite distractor mechanisms mounted to a frame. The distractor mechanisms each include an adjustment mechanism permitting the distractor mechanism to be pivoted relative to the vertebra and secured to the frame after being repositioned.

28 Claims, 8 Drawing Sheets

U.S. PATENT DOCUMENTS

| | | | |
|---|---|---|---|
| 5,353,784 A | 10/1994 | Nady-Mohamed | |
| 5,389,080 A | 2/1995 | Yoon | |
| 5,490,819 A | 2/1996 | Nicholas et al. | |
| 5,503,617 A | 4/1996 | Jako | |
| 5,509,893 A | 4/1996 | Pracas | |
| 5,512,038 A | 4/1996 | O'Neal et al. | |
| 5,549,595 A | 8/1996 | Freitas | |
| 5,573,517 A | 11/1996 | Bonutti et al. | |
| 5,618,260 A | 4/1997 | Caspar et al. | |
| 5,667,481 A | 9/1997 | Villalta et al. | |
| 5,674,240 A | 10/1997 | Bonutti et al. | |
| 5,681,265 A | 10/1997 | Maeda et al. | |
| 5,688,223 A | 11/1997 | Rosendahl | |
| 5,707,359 A | 1/1998 | Bufalini | |
| 5,728,046 A * | 3/1998 | Mayer et al. | 600/210 |
| 5,755,732 A | 5/1998 | Green et al. | |
| 5,776,054 A | 7/1998 | Bobra | |
| 5,779,629 A | 7/1998 | Hohlen | |
| 5,785,648 A | 7/1998 | Min | |
| 5,795,291 A | 8/1998 | Koros et al. | |
| 5,813,978 A | 9/1998 | Jako | |
| 5,823,947 A | 10/1998 | Yoon et al. | |
| 5,865,731 A | 2/1999 | Lenox et al. | |
| 5,888,196 A | 3/1999 | Bonutti | |
| 5,928,139 A | 7/1999 | Koros et al. | |
| 5,931,777 A | 8/1999 | Sava | |
| 5,944,658 A * | 8/1999 | Koros et al. | 600/232 |
| 5,951,466 A | 9/1999 | Segermark et al. | |
| 5,961,499 A | 10/1999 | Bonutti et al. | |
| 5,976,146 A | 11/1999 | Ogawa et al. | |
| 6,027,518 A | 2/2000 | Gaber | |
| 6,042,540 A | 3/2000 | Johnston et al. | |
| 6,074,380 A | 6/2000 | Byrne et al. | |
| 6,083,154 A * | 7/2000 | Liu et al. | 600/234 |
| 6,096,046 A | 8/2000 | Weiss | |
| 6,099,547 A | 8/2000 | Gellman et al. | |
| 6,139,493 A | 10/2000 | Koros et al. | |
| 6,149,583 A | 11/2000 | Vierra et al. | |
| 6,162,236 A | 12/2000 | Osada | |
| 6,171,299 B1 | 1/2001 | Bonutti | |
| 6,187,000 B1 | 2/2001 | Davison et al. | |
| 6,200,322 B1 | 3/2001 | Branch et al. | |
| 6,296,609 B1 | 10/2001 | Brau | |
| 6,312,443 B1 | 11/2001 | Stone | |
| 6,325,812 B1 | 12/2001 | Dubrul et al. | |
| 6,361,492 B1 | 3/2002 | Santilli | |
| 6,371,911 B1 | 4/2002 | Hossain et al. | |
| 6,431,025 B1 | 8/2002 | Koros et al. | |
| 6,605,088 B1 * | 8/2003 | St. Onge et al. | 606/54 |
| 6,616,605 B2 | 9/2003 | Wright et al. | |
| 2002/0161368 A1 * | 10/2002 | Foley et al. | 606/61 |
| 2003/0149341 A1 * | 8/2003 | Clifton | 600/210 |
| 2003/0153910 A1 * | 8/2003 | Janowski et al. | 606/56 |
| 2004/0002629 A1 | 1/2004 | Branch et al. | |

FOREIGN PATENT DOCUMENTS

| | | |
|---|---|---|
| DE | 8704901 U * | 7/1987 |
| EP | 1 192 905 | 9/2001 |
| FR | 1 019 217 A | 1/1952 |
| FR | 2 788 958 | 8/2000 |
| FR | 2 807 313 | 10/2001 |

* cited by examiner

DISTRACTION AND RETRACTION SYSTEM FOR SPINAL SURGERY

CROSS-REFERENCE TO RELATED APPLICATION

This application claims the benefit of the filing date of Provisional Application Ser. No. 60/428,800, filed on Nov. 23, 2002.

BACKGROUND

Surgeons have employed retractors formed by plates to retract tissue and provide access to a surgical site. These retractors are manually inserted by shifting aside the blood vessels, the nerves and the soft tissues by means of their end portions that are positioned adjacent to the spine. The retractors may be completed by pins which have ends inserted in the spine. The retractors can slide along these pins. Another technique teaches connecting the retractors about a frame so as to maintain them in the desired position and clear the operating area between the retractors.

Prior devices are not fully convenient to use in spinal surgery, in particular for positioning and maintaining retractors in a desired angular orientation relative to the operating space, in providing and maintaining an operating space in a posterior lateral approach, or for maintaining distraction of adjacent vertebrae. In addition, these prior systems are not fully compatible with spinal stabilization procedures both in the disc space and exteriorly of the disc space. Further, the design of such systems may require tissue retraction and exposure beyond that which may be desirable to minimize trauma to the patient as a result of the surgical procedure.

Thus, there is a need for systems for spinal surgery that facilitate distraction of adjacent vertebrae while maintaining tissue retraction and minimizing the invasiveness of the procedure.

SUMMARY

Surgical instrumentation systems are provided that particularly, but not exclusively, relate to instrumentation for retracting and shifting aside soft tissues and vessels and also for maintaining distraction of bony structures for the purpose of spinal surgery. In one application, distractor maintenance mechanisms are pivotally adjustable relative to the bony structure to which each is engaged to reduce the invasiveness of the procedure and facilitate instrument placement at the operative site through the operative approach formed by the surgical instrumentation system.

According to one aspect, the surgical instrumentation system is adapted for a posterior lateral approach to the spine. It is further contemplated that the surgical instrumentation system has application in other approaches to the spine, either in the posterior-lateral configuration or in an alternative configuration.

According to another aspect, a surgical instrumentation system for providing access to the patient's spine includes a frame and at least one retractor attached to a frame. First and second distractor mechanisms are engageable to respective ones of first and second anchors engaged to adjacent vertebrae. The distractor mechanisms are pivotal relative to the vertebra to which each is mounted, and can be coupled to the frame to provide a rigid construct between the anchor and the frame to maintain distraction of the adjacent vertebrae.

According to a further aspect, a surgical instrumentation system to provide access to the patient's spine includes a frame and a pair of retractors attached to the frame. The frame includes a first portion lying in a first plane and a second portion lying in a second plane, the second plane forming an angle with the first plane. In the operative position of the frame, a medial retractor is attached to the first portion and positionable in an incision adjacent the midline of the spinal column. A lateral retractor is attached to the second portion of the frame and positioned in the incision along a posterior lateral approach to the disc space.

In another aspect, surgical instrumentation to provide access to a patient's spine includes a frame and a number of distractor mechanisms attached to the frame. A first distractor mechanism is engaged to bony structure with a first anchor at its distal end. A second distractor mechanism is coupled at its distal end to a second anchor that is engaged to bony structure. The first and second anchors allow the first and second distractor mechanisms to be pivoted relative to the vertebrae.

In a further aspect, a surgical instrumentation system includes a frame and first and second distractor mechanisms mounted to anchors engaged to respective ones of first and second vertebrae. Adjustment mechanisms are provided to attach the first and second distractor mechanisms to the frame. The adjustment mechanisms are movable from a first condition in locking engagement with the distractor mechanisms to a second condition permitting the distractor mechanisms to pivot relative to the vertebrae.

Methods for performing spinal surgery are also contemplated. An incision is made for access to a spinal disc space. At least one retractor is positioned in the incision and engaged to a frame. Cephalad and caudal distractor mechanisms are coupled to anchors engaged to vertebrae on each side of the target disc space. The disc space is distracted and the cephalad and caudal distractor mechanisms are coupled to the frame to maintain distraction. Further distraction or compression of the adjacent vertebrae can be effected through manipulation of the cephalad and caudal distraction mechanisms.

Further objects, features, forms, benefits, aspects, and advantages will appear from the following description, with reference to the accompanying drawings.

DESCRIPTION OF ILLUSTRATED EMBODIMENTS

Figure 1:
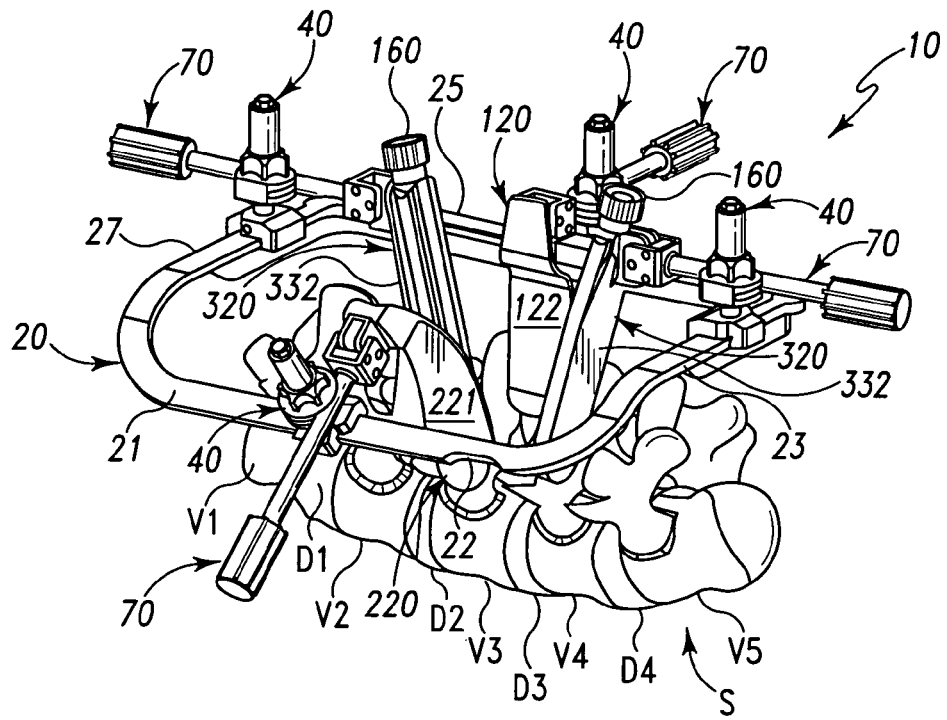
FIG. 1 is a perspective view of a surgical instrumentation system positioned to provide access to the spine.
Figure 4:
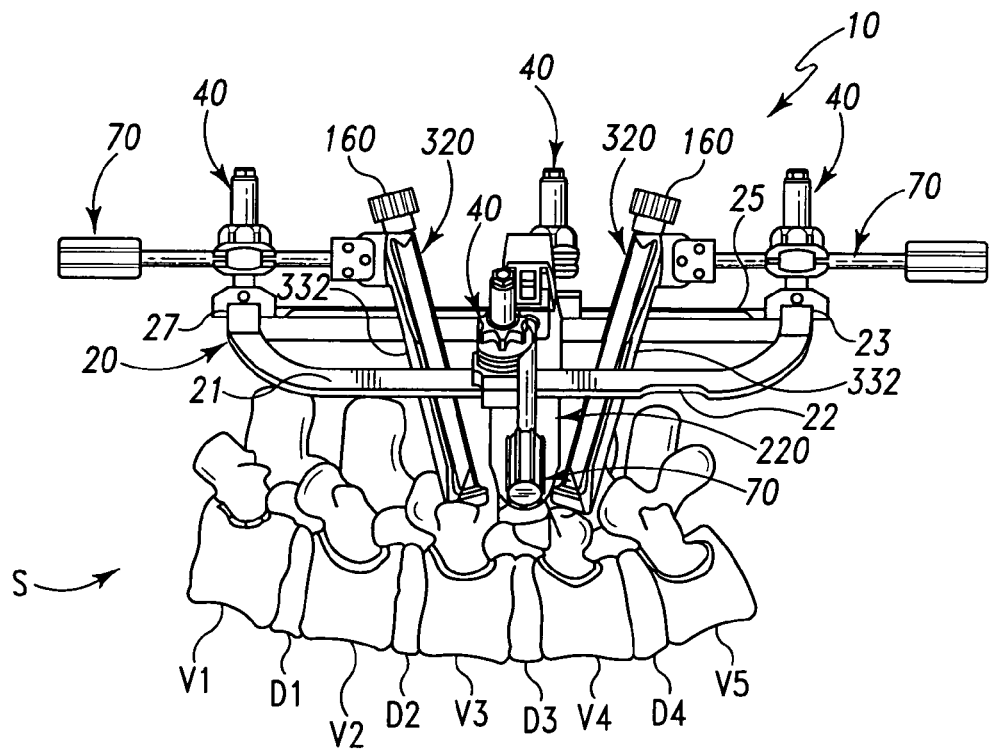
FIG. 4 is an elevation view of the surgical instrumentation system of FIG. 1 looking cephaladly along the spine.
Figure 2:
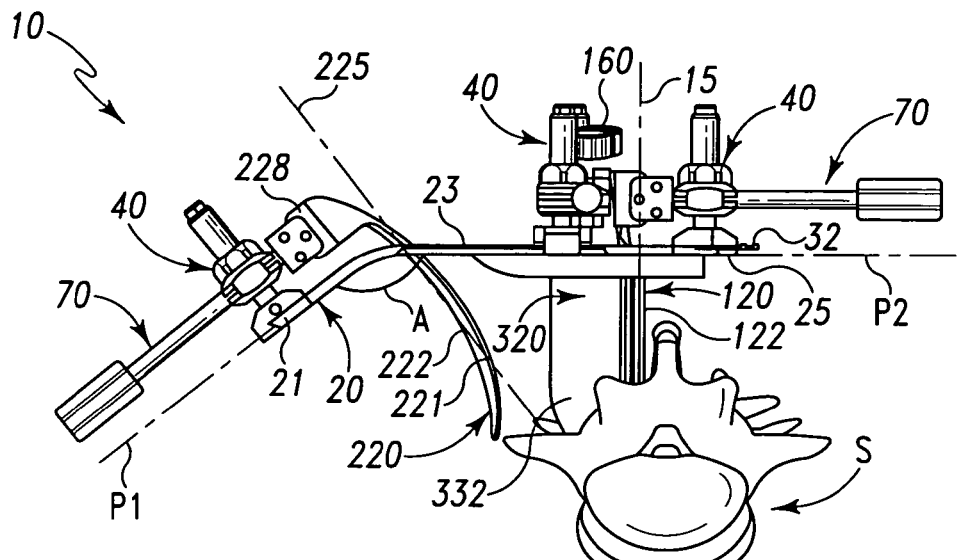
FIG. 2 is a side view of the surgical instrumentation system and spinal column segment of FIG. 1 looking medially toward the spine.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The surgical instrumentation system 10 illustrated in the figures is adapted to enable a surgeon to effect retraction and shifting aside of soft tissues, muscles, and vessels so as to clear an operating area on the spine while simultaneously maintaining a distraction of adjacent bony portions, such as adjacent vertebrae, of the spinal column. Surgical instrumentation system 10 provides an operative approach to the spine for a subsequent surgical intervention such as, for example, to installing spinal prostheses or stabilization systems in a disc space between adjacent vertebrae or exteriorly between vertebrae. In one specific application, surgical instrumentation system 10 provides a posterior lateral operative approach in order to, for example, provide access to the disc space for distraction, removal of disc material and bone material, and insertion of spinal implants. Surgical instrumentation system 10 also has application in other approaches to the spinal column to provide access to one or more spinal disc spaces or bony structures of the vertebrae.

Surgical instrumentation system 10 is shown in one operative orientation relative to a spinal column segment S in FIGS. 1-6. The spinal column segment S includes vertebrae V1, V2 with disc space D1 therebetween; vertebrae V2, V3 with disc space D2 therebetween; vertebrae V3, V4 with disc space D3 therebetween; and vertebrae V4, V5 with disc space D4 therebetween. Spinal column segment S can comprise the lumbar region of the spine; however, it is contemplated that surgical instrumentation system includes applications in other regions of the spine, including the thoracic, cervical and sacral regions. Surgical instrumentation system 10 is further shown positioned relative to spinal column segment S to provide access to disc space D3 between vertebrae V3, V4, which can correspond to the L3 and L4 vertebrae. Surgical instrumentation system 10 can also be positioned to provide access to one or more disc spaces, to disc spaces between other vertebrae of the spine, and in operative orientations other than a posterior-lateral approach.

Surgical instrumentation system 10 comprises a frame 20 having at least one of two retractors 120 and 220 and a pair of distractor mechanisms 320 releasably attachable thereto. Each retractor 120 and 220 includes a blade portion 122 and 221, respectively, for shifting aside soft tissues and blood vessels. Distractor mechanisms 320 are mounted to respective vertebrae of spinal column segment S, and may include a retractor portion 332 adapted to contact and retract adjacent tissue. In its illustrated operative position relative to the patient for a posterior lateral approach, retractor 120 is positioned medially adjacent the midline or posterior elements of the spinal column segment S, and retractor 220 is positioned laterally or postero-laterally relative to the spinal column segment S. Embodiments are further contemplated in which retractor 220 is not provided, but rather a single medial retractor 120 is provided and attached to frame 20.

Figure 5:
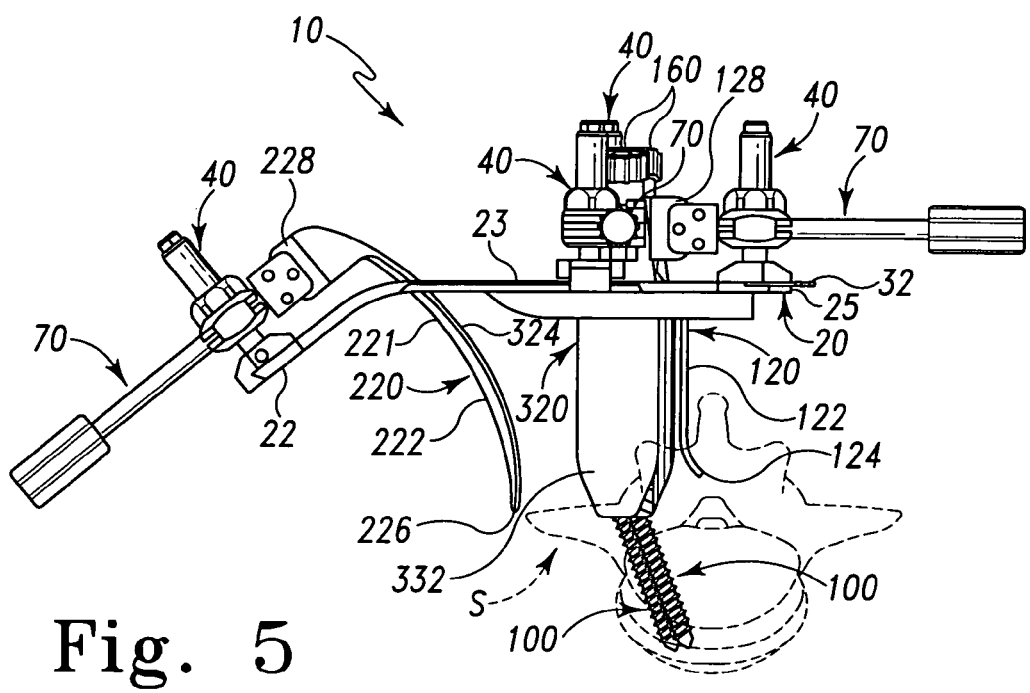
FIG. 5 is the view of FIG. 4 showing anchors attaching the cephalad and caudal distractor mechanisms to vertebrae of the spine.

In FIGS. 1-6 surgical instrumentation system 10 includes a pair of distraction mechanisms 320 secured to respective ones of the vertebrae V3, V4. Distraction mechanisms 320 can be movable attached to frame 20. As shown in FIG. 5, distraction mechanisms 320 can be secured to vertebrae V3, V4 with anchors 100 engaged to respective ones of vertebrae V3, V4. In the illustrated embodiment, anchors 100 are multi-axial screws engaged in the pedicles of the vertebrae V3, V4. Some examples of multi-axial screws having application herewith are described in U.S. Pat. Nos. 5,797,911 and 5,879,350, each of which is incorporated herein by reference. Other techniques employing surgical instrumentation system 10 contemplate other forms for anchors 100, such as uni-axial bone screws, staples, interbody devices, suture anchors, clamps, hooks or bolts, or other anchor device, for example. It is also contemplated that anchors 100 can be engaged to other portions of vertebrae V3, V4, such as the facets, the anterior portion of the vertebral body, or any posterior elements of the vertebrae. Anchors 100 can be engaged bi-cortically or uni-cortically to bony elements, or to soft tissue elements.

In the operative position illustrated in FIGS. 1-6, frame 20 includes a lateral member 21, a caudal member 23, a medial member 25, and a cephalad member 27. At least one recess 22, 24, 26, 28 is formed in each of the members 21, 23, 25, 27 to accommodate attachment of a clamping device 40 thereto, as discussed further below. Each retractor 120, 220 and distractor mechanism 320 is attached to frame 20 by a respective one of the clamping mechanisms 40 and adjustment mechanisms 70, as discussed further below. Members 21, 23, 25, 27 can be integrally formed with one another to provide frame 20 in the form of a ring which completely encircles an opening 30. Opening 30 is sized to accommodate placement of the retractors 120, 220 and distractor mechanisms 320 therein while also providing space to access the surgical site through the operative approach formed between the retractors 120, 220 and distractor mechanisms 320.

In one embodiment, frame 20 includes lateral member 21 that lies in plane P1 and medial member 25 that lies in plane P2. Plane P2 forms angle A with plane P1. When positioned on the patient to provide a posterior-lateral operative approach, medial member 25 extends along the posterior side of the patient while lateral member 21 extends along the posterior-lateral side of the patient. Angle A allows the members 21, 25 of frame 20 to follow the patient anatomy, and also allows optimal positioning of retractors 120, 220 on the frame and relative to the patient to provide a posterior lateral access path to the spinal disc space. In one embodiment, angle A is about 30 degrees. Caudal and cephalad members 23, 27 are parallel and extend between lateral and medial members 21, 25 and provide a transition between planes P1 and P2. Other embodiments contemplate angle A ranging from 0 degrees to 90 degrees.

In addition, cephalad member 27 and caudal member 23 include at least a portion lying in plane P2, allowing attachment of distraction mechanisms 320 to frame 20 in the same plane as medial retractor 120. When attached to frame 20 and anchors 100, distraction mechanisms 320 can maintain a distraction provided between vertebrae V3 and V4 to restore disc space D3 to a desired disc space height. Such distraction can be achieved with a distraction instrument positioned in the disc space prior to securing distraction mechanisms 320 to frame 20. Such distraction can also be achieved by applying distraction forces to anchors 100 either directly, or through extensions coupled to anchors 100 prior to securement of distraction mechanisms 320 to frame 20.

In a further form, the laterally positioned retractor 220 can be eliminated, and tissue retraction along the posterior lateral side is maintained by the tissue displacement provided by and between the laterally oriented sides of distraction mechanisms 320. Frame 20 can also be provided in a form in which each member thereof lies in the same plane. Other shapes for frame 20 are also contemplated. For example, frame 20 can be circular, rectangular, square, elliptical or U-shaped. In embodiments eliminating retractor 220, frame 20 can be provided with an open side formed by omitting lateral member 21, for example. Frame 20 may further be provided with one or more brackets 32 to enable the surgeon to attach frame 20 to an arm secured to the surgical table to support instrumentation system 10 in its operative position. In the illustrated embodiment, a bracket 32 is provided at each corner of frame 20 positioned along the spinal mid-line.

Medial retractor 120 includes an elongated blade portion 122 extending proximally from a distal end portion 124. Blade portion 122 can include a relatively flat profile along its medially oriented tissue contacting surface and its opposite laterally oriented surface which extends along the operative approach to the spinal column. However, curved surfaces are also contemplated. Distal end portion 124 is curved medially from blade portion 122, and is positionable along or against the posterior bony structures of the vertebrae, such as the spinous processes. Blade portion 122 includes a width that retains tissue, and vessels away from the approach formed between the retractors and distractor mechanisms of surgical instrumentation system 10. Blade portion 122 is generally linear along its longitudinal axis between distal end portion 124 and proximal end portion 126. Proximal end portion 126 is offset from and extends generally parallel to blade portion 122. Proximal end portion 126 is offset laterally relative to blade portion 122 to facilitate placement of blade portion 122 and distal end portion 124 more medially relative to the operative approach when proximal end portion 126 is coupled to frame 20. Proximal end portion 126 includes flanges 128 for engaging adjustment mechanism 70, as discussed further below. Retractor 220 similarly includes flanges 228 at its proximal end for engaging an adjustment mechanism 70.

Figure 3:
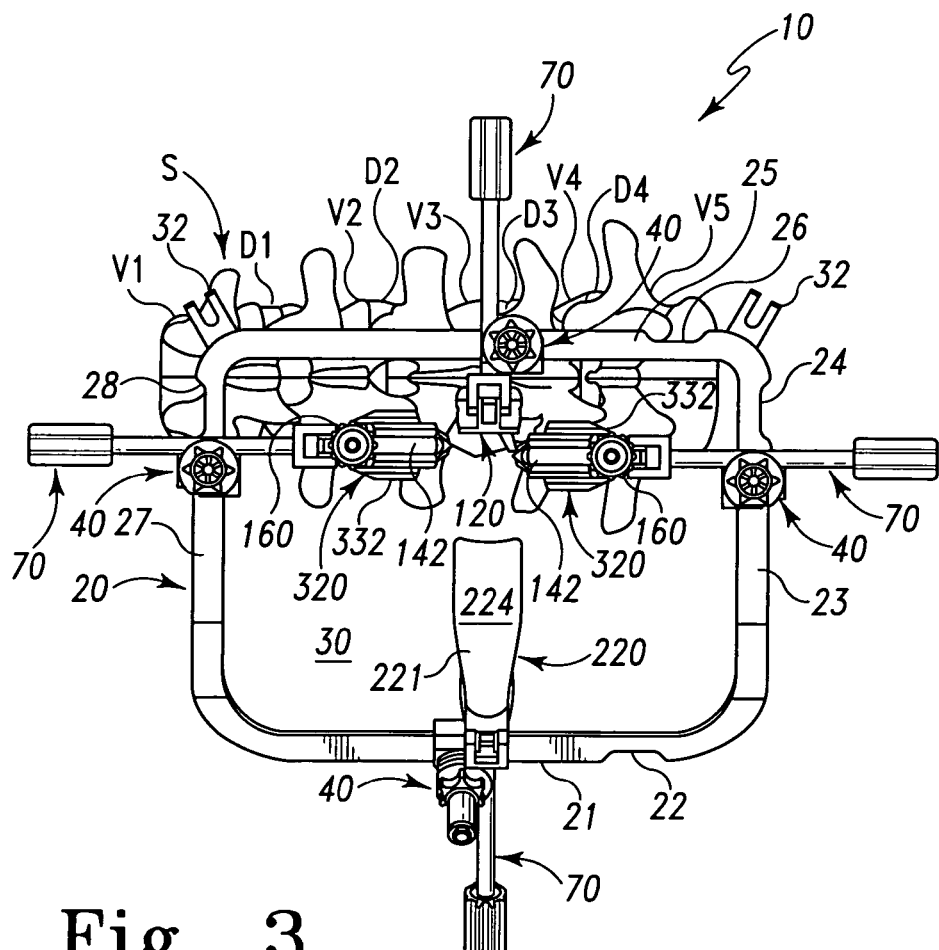
FIG. 3 is a view looking down at the surgical instrumentation system of FIG. 1 along the approach formed to the spine with it.

Lateral retractor 220 is formed by an elongate blade portion 221 extending along longitudinal axis 225. Blade portion 221 includes a lower laterally oriented tissue contacting surface 222 concavely curved along longitudinal axis 225 and positionable against the tissue to be retracted. Blade portion 221 of retractor 220 includes an opposite medially oriented support surface 224 convexly curved along longitudinal axis 225. Support surface 224 is oriented toward the operative approach formed by surgical instrumentation system 10. As shown in FIG. 3, support surface 224 of retractor 220 includes a concave curvature across its width and transversely to longitudinal axis 225, forming a slight U-shape that can accommodate and support surgical instruments positioned therealong. Retractor 220 further includes a lower distal end portion 226 tapering in width along longitudinal axis 225 toward the distal tip of blade portion 221 to minimize its intrusion into the surrounding tissue. The curvature of blade portion 221 of lateral retractor 220 also positions its distal end away from the access opening formed into the disc space, providing greater tissue retraction in this area and additional room to accommodate placement of surgical instruments, implants and devices between and along the vertebrae.

Figure 7:
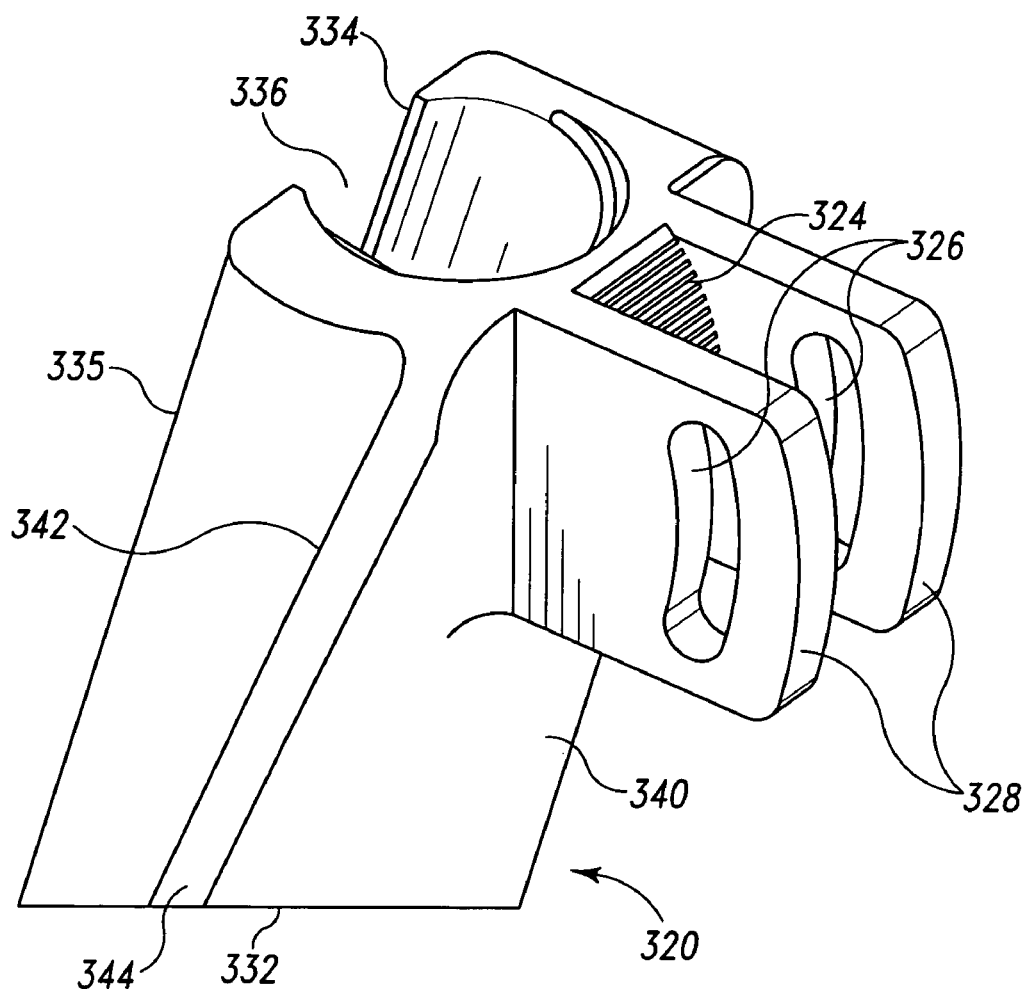
FIG. 7 is a perspective view of a proximal portion of a retractor portion of the distractor mechanism comprising a portion of the surgical instrumentation system.
Figure 8:
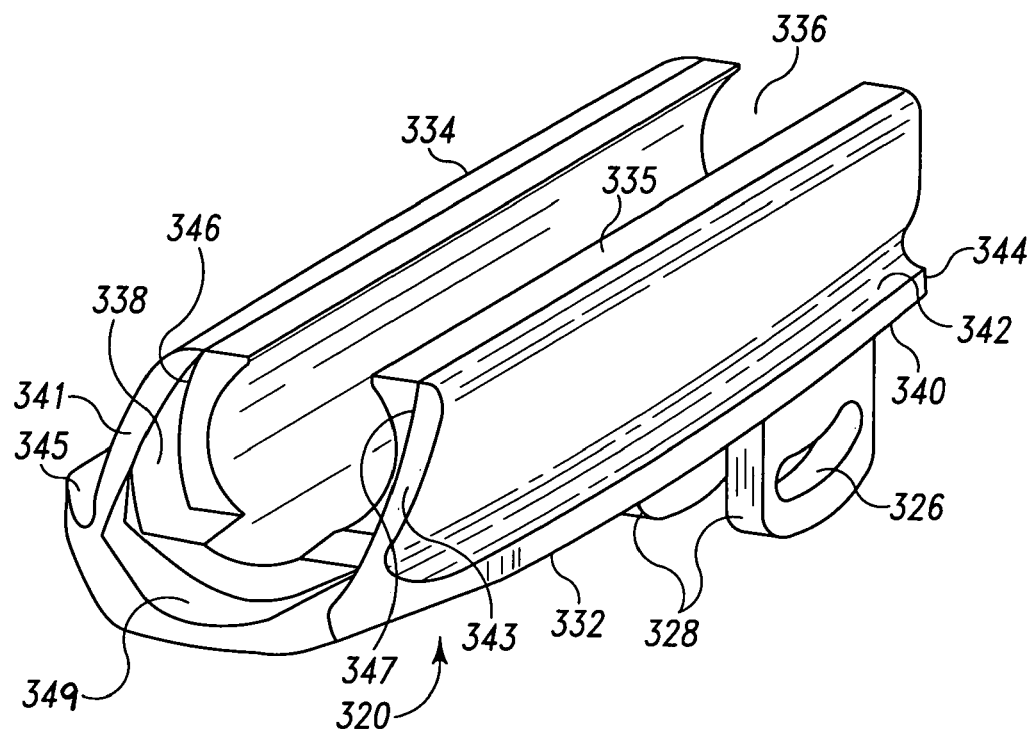
FIG. 8 is a perspective view looking at a distal end of the retractor portion of the distractor mechanism of the surgical instrumentation system.

Surgical instrumentation system 10 includes distraction mechanisms 320 mountable to respective ones of the cephalad and caudal members 27, 23 of frame 20 and also to respective ones of the anchors 100. Distractor mechanisms 320 each include retractor portion 332 mountable to an anchor extension 142 extending from respective ones of the anchors 100. As shown in further detail in FIGS. 7 and 8, retractor portion 332 includes a tissue contacting surface 340 that is convexly curved between the opposite lateral sides 344, 345 of retractor portion 332. Retractor portion 332 includes an opposite surface 349, which includes a pair of arms 334, 335 projecting therefrom and extending therealong that form a receptacle 336 therebetween. Arms 334, 335 can each define a concave inner surface and outer ends that project toward one another to provide receptacle 336 with a form that slidably captures anchor extension 142 therein.

Figure 9:
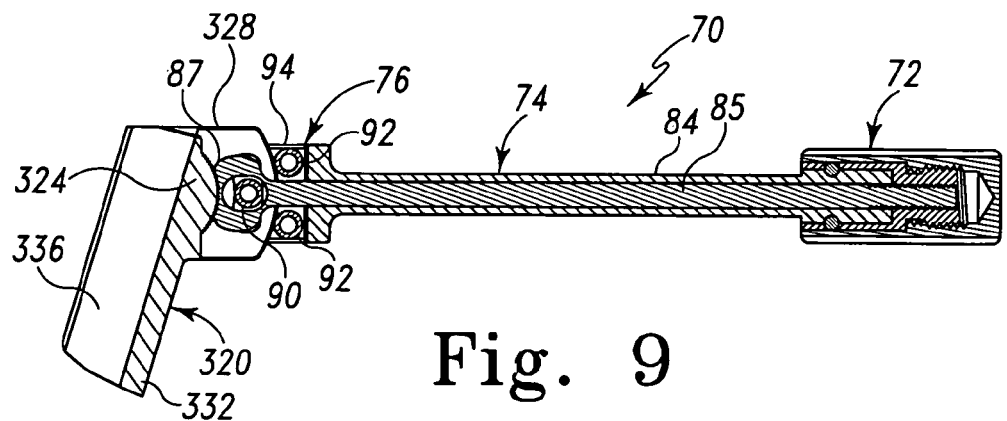
FIG. 9 is a sectional view of an adjustment mechanism engaged with a proximal portion of a distractor blade comprising a portion of the surgical instrumentation system.
Figure 10:
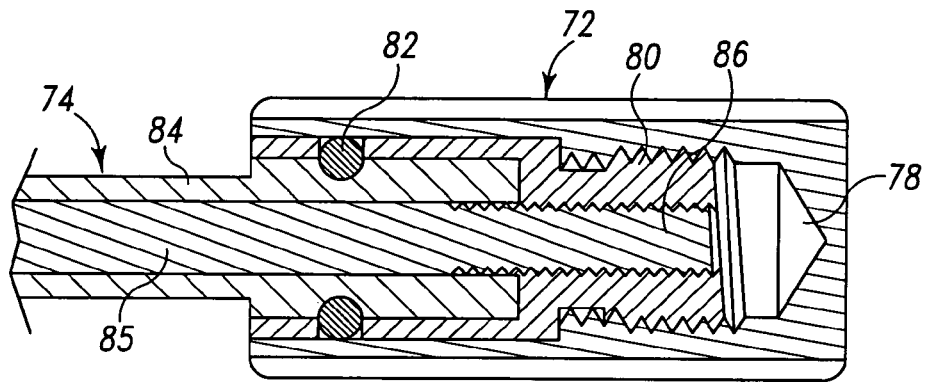
FIG. 10 is an enlarged view of a proximal end of the adjustment mechanism of FIG. 9.
Figure 11:
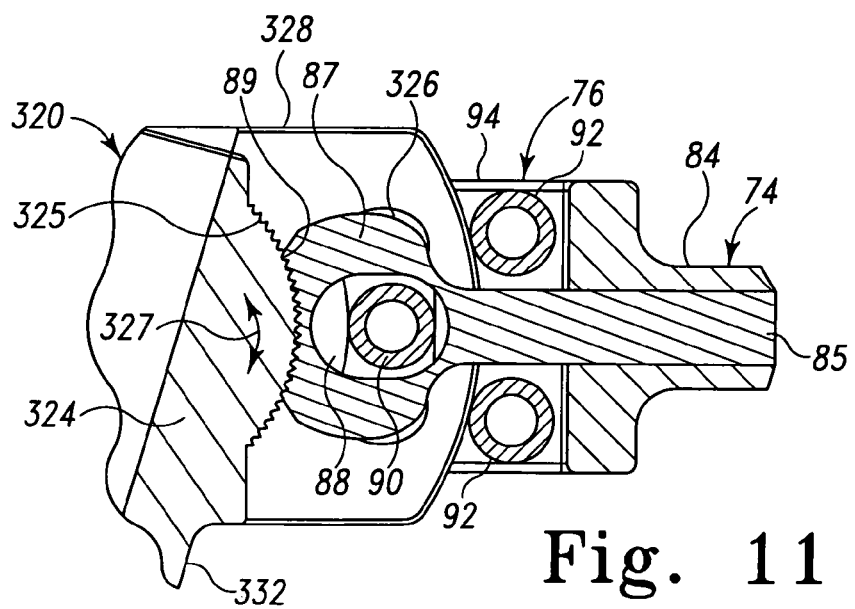
FIG. 11 is a sectional view of the connection of the adjustment mechanism with the retractor portion of the distractor mechanism.

Retractor portion 332 further includes a proximal end adapted to be pivotally coupled with adjustment mechanism 70, as shown in FIGS. 9-11. In the illustrated embodiment, this configuration includes flanges 328 projecting from tissue contacting surface 340 in a direction opposite arms 334, 335. Each flange 328 includes an arcuate slot 326 extending therethrough and aligned with one another to receive a pin to pivotally couple retractor portion 332 to adjustment mechanism 70. Slots 326 define a range of positions along which distractor mechanism 320 can be repositioned relative to the vertebra to which it is coupled. An engagement member 324 is positioned between flanges 328, and includes a number of teeth 325 along a convexly curved surface thereof for selective and locking engagement with adjustment mechanism 70, as discussed further below.

Adjustment mechanisms 70 provide a pivotal coupling arrangement with each of the retractors 120, 220 and distractor mechanisms 320 that facilitates pivotal adjustment of the retractors 120, 220 and distraction mechanisms 320 in their operative position in the patient. Adjustment mechanism 70 will be described with reference to distractor mechanisms 320, it being understood that retractors 120, 220 may include a similar proximal end configuration with flanges for coupling with the adjustment mechanism 70 extending therefrom.

Adjustment mechanism 70 includes an adjustment handle 72 and a shaft assembly 74 extending from adjustment handle 72 toward distractor mechanism 320. Shaft assembly 74 extends to a coupling assembly 76 opposite adjustment handle 72. Coupling assembly 76 includes side plates 94 having upper and lower abutment rollers 92 extending therebetween. A pivot roller 90 extends between plates 96, and also through slots 326 of flanges 328 of retractor portion 332. Pivot roller 90 pivotally couples retractor portion 332 to a distal end of adjustment mechanism 70.

Shaft assembly 74 includes an outer shaft 84 and an inner shaft 85 positioned therethrough. Inner shaft 85 includes an engagement member 87 at a distal portion thereof. Engagement member 87 includes a number of teeth 89 at a distal end thereof that interdigitate with teeth 325 of engagement member 324 of retractor portion 332. The distal end of engagement member 87 includes a concave profile adapted to receive the convexly curved profile of the adjacent surface of engagement member 324. The interdigitating concave-convex surfaces facilitate locking a position of retractor portion 332 after pivoting movement of retractor portion 332, as indicated by arrows 327, when engagement members 87, 324 are disengaged from one another.

When the desired orientation of distractor mechanism 320 (or retractors 120, 220) has been obtained with pivotal adjustment, engagement member 87 can then be engaged to engagement member 324 at any one of a number of positions defined by the interdigitating teeth 89, 325. The concave-convex mating surface profiles allow all of the teeth to interdigitate in the engaged position at any orientation of distractor mechanism 320, providing rigidity between the adjustment mechanism 70 and the retractor or distractor mechanism to which it is engaged. The rigidity of the engagement between adjustment mechanism 70 and distractor mechanism 320 is further enhanced by abutment rollers 92 contacting the ends of the adjacent flanges 328 and with pivot roller 90 restraining flange members 328 therebetween.

To facilitate engagement and disengagement of the engagement members 87, 324, engagement member 87 includes a slot 88 through which pivot roller 90 extends. Pivot roller 90 is free to travel longitudinally along slot 88 as engagement member 87 and inner shaft 85 are longitudinally moved with adjustment handle 72. Accordingly, adjustment handle 72 is operable to selectively release and engage engagement member 87 with engagement member 324.

As shown in FIG. 10, adjustment handle 72 includes an internal cavity 78 that receives a linking member 80. Adjustment handle 72 is threadingly engaged to a proximal portion of linking member 80, and can be locked thereto with a locking thread configuration, epoxy or other suitable locking arrangement. A distal portion of linking member 80 is rotatably positioned about a proximal end of outer shaft 84. A number of bearings 82 rotatably couple linking member 80 and adjustment handle 72 about outer shaft 84. Linking member 80 further includes an inner passage extending therethrough, which is configured along the proximal portion of linking member 80 to threadingly engage a proximal end 86 of inner shaft 85.

Adjustment handle 72 and linking member 80 can be rotated about the proximal end 86 of inner shaft 85. The threaded engagement between inner shaft 85 and linking member 80 moves inner shaft 85, and thus engagement member 87, distally and proximally in accordance with the particular thread turn provided between inner shaft 85 and linking member 80. Engagement member 87 can accordingly be moved along roller 90 and into and out of engagement with engagement member 324 in accordance with the direction of rotation of adjustment handle 72.

Figure 12:
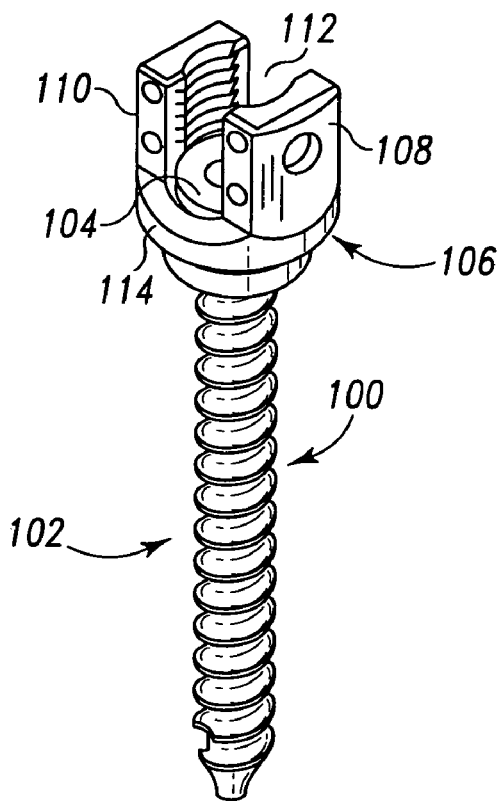
FIG. 12 is a perspective view of one embodiment bone anchor.

Referring back to FIG. 8, retractor portion 332 includes a distal end configured to receive a proximal end of anchor 100 therein such that retractor portion 332 is fixedly secured to anchor 100. In FIG. 12, anchor 100 is shown as a multi-axial screw having a lower threaded shaft 102 for engaging bony structure and a proximal head 104. The proximal portion of anchor 100 can comprise a yoke 106 pivotally coupled to head 104. Yoke 106 includes a pair of arms 108, 110 defining a U-shaped passage 112 therebetween to receive a stabilization device, such as a spinal rod or tether. Arms 108, 110 can further be internally threaded to receive a set screw to retain the stabilization device in passage 112.

Arms 108, 110 of yoke 106 are received and firmly seated in a socket portion 338 of retractor portion 332 when distractor mechanism 320 is engaged to anchor 100. Socket portion 338 is formed by distal ends 346, 347 of respective ones of the arms 334, 335, and by distal extensions 341, 343 of the outer portions of arms 334, 335. Distal extensions 341, 343 are recessed relative to arms 334, 335 along receptacle 336 so that arms 108, 110 of yoke 106 can be positioned in socket portion 338 with passage 112 remaining substantially unobstructed. So positioned, arms 108, 110 form an extension of the adjacent arm 334, 335, and passage 112 is aligned with receptacle 336. The yoke 106 is firmly and non-pivotally seated in socket portion 338, while yoke 106 is allowed to pivot relative to shaft 102. Retractor portion 332 further includes a distal lip 349 extending distally of socket portion 338 and positionable along seat 114 of yoke 106.

Figure 14:
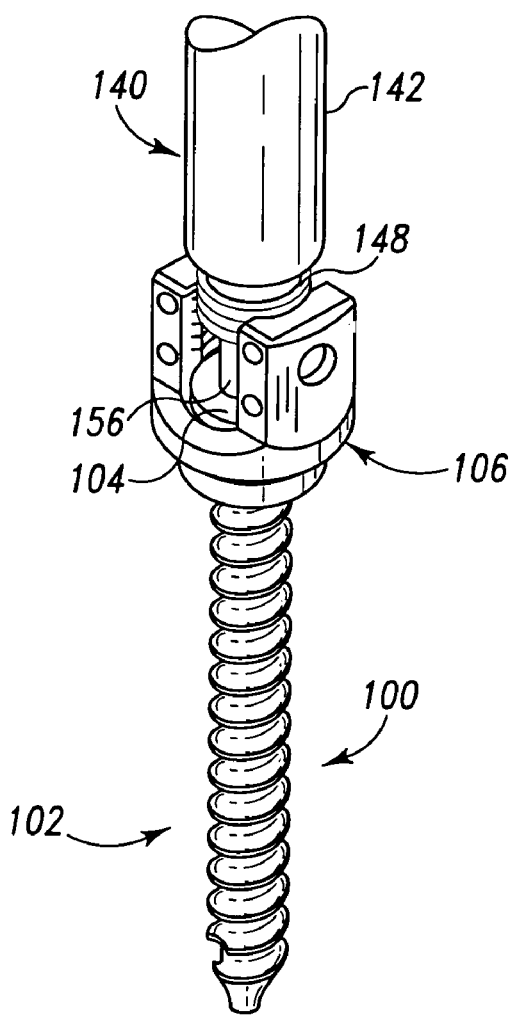
FIG. 14 is a perspective view of the engagement of the driving instrument assembly with the bone anchor.
Figures 13, 15:
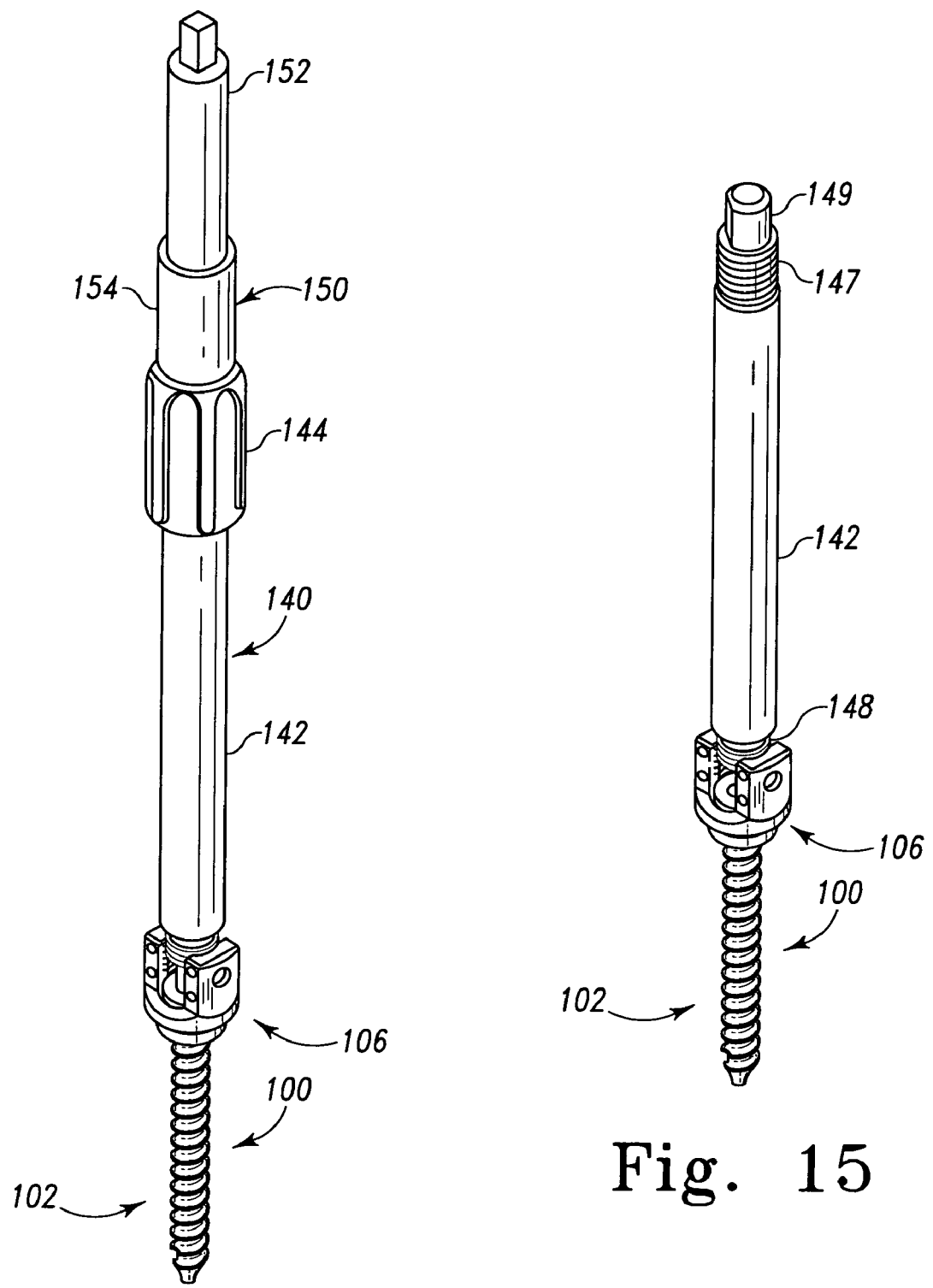
FIG. 13 is a perspective view of a driving instrument assembly engaged to the bone anchor of FIG. 12.
FIG. 15 is a perspective view with an extender of the driving instrument assembly attached to the bone anchor and a driver instrument of the driving instrument assembly removed.

It is further contemplated that anchor extension 142 may comprise a portion of a driving instrument assembly that can be engaged to anchor 100 to facilitate engagement of anchor 100 to the bony structure. As shown in FIGS. 13-15, a driving instrument assembly 140 is engaged to anchor 100, and is operable by the surgeon to engage threaded shaft 102 to a bony structure. Threaded shaft 102 can be provided in a form suitable for self-drilling into the bone during placement, for self-tapping a pre-drilled bore, or for positioning in a pre-drilled and pre-tapped bore in the bony structure.

Driving instrument assembly 140 includes a cylindrical anchor extension 142 and driver instrument 150 removably positioned through a longitudinal passage of anchor extension 142. Anchor extension 142 includes a distal extension 148 threadingly engageable between arms 108, 110 of yoke 106. Driving instrument 150 includes a driving instrument coupler 144 to facilitate attachment and removal of driving instrument 150 to anchor extension 142. Driving instrument 150 includes a shaft 152 extending through and rotatably coupled to a sleeve 154 of coupler 144 with a number of bearings. Shaft 152 is further allowed to axially translate relative to coupler 144 and anchor extension 142 within a limited range defined by the interconnection between shaft 152 and sleeve 154. Driving instrument 150 includes a proximal extension 152 with a tool engagement portion at a proximal end thereof. As shown in FIG. 14, driving instrument 150 includes a distal end 156 projecting from anchor extension 142 for engaging a tool recess in head 104 of anchor 100.

In use, driving instrument 150 is inserted through and engaged to anchor extension 142, and its distal end 156 is positioned in the tool recess in head 104 of anchor 100. Anchor extension 142 is threadingly engaged to yoke 106. Driving instrument 150 is rotatable relative to anchor extension 142 with a driving instrument engaged to the proximal end of shaft 152. When the anchor 100 has been suitably engaged to the bony structure, driving instrument 150 can be removed from anchor extension 142 by detaching coupler 144 from anchor extensions 142. Retractor portion 332 of distraction mechanism 320 can then be loaded onto anchor extension 142 with anchor extension 142 in receptacle 336.

Retractor portion 332 can be secured to anchor extension 142 with a second coupling member 160 engaged to proximal end 147 of anchor extension 142 (FIGS. 1-6 and 15.) Coupling member 160 contacts the proximal end of retractor portion 332 to push and retain socket portion 338 into contact with yoke 106 of anchor 100 and firmly couple the retractor portion 332 thereto. However, yoke 106 can still be pivoted relative to shaft portion 102 of anchor 100, permitting distractor mechanism 320 to be pivotally adjustable in position relative to the vertebra to which it is mounted. Anchor extension 142 is provided with a proximal tool engagement portion 149 to facilitate removal of anchor extension 142 from anchor 100 if necessary.

In another embodiment, distractor mechanism 320 does not include a retractor portion 332, but rather the anchor extension portion of the distractor mechanism contacts and retracts the adjacent tissue. Such a modified distractor mechanism can be employed with frame 20 with an opposite distractor mechanism, and a medial retractor 120 alone or in combination with a lateral retractor 220.

Figure 6:
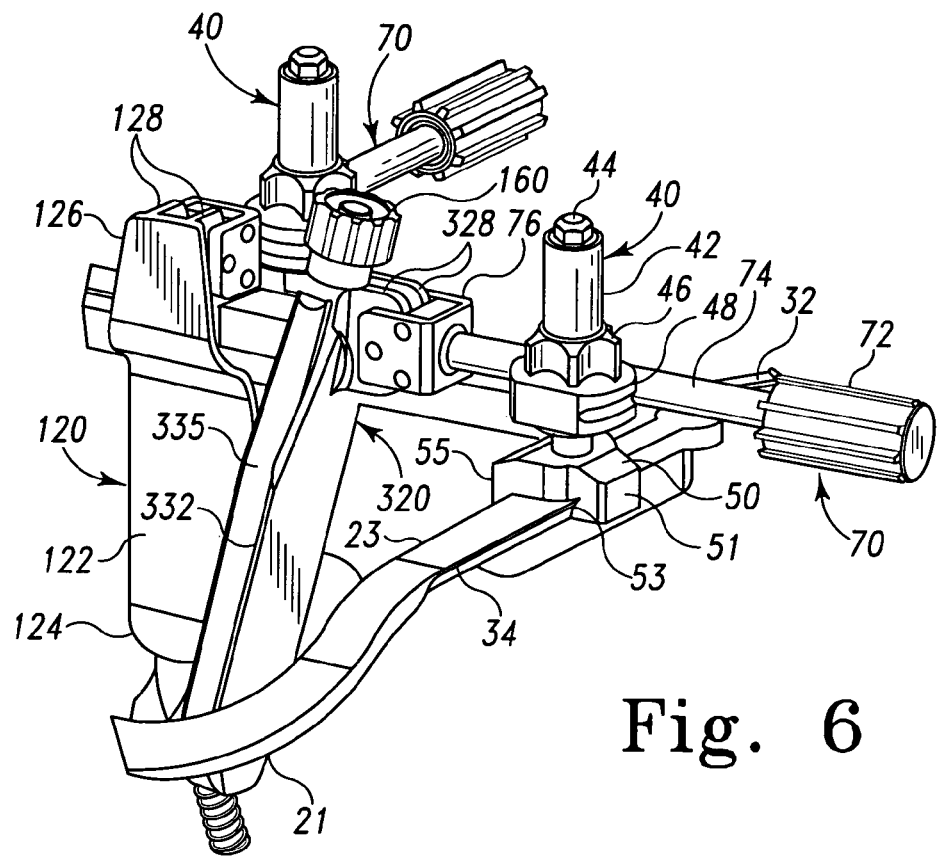
FIG. 6 is a perspective view of the medial retractor and caudal distractor mechanism of the surgical instrumentation system of FIG. 1.

In order to secure retractors 120, 220 and distractor mechanisms 320 to frame 20, a number of clamping devices 40 are provided that releasably engage the corresponding adjustment mechanism 70 extending from the retractors 120, 220 and distractor mechanisms 320. As shown in FIG. 6, and in further detail in FIG. 16, clamping device 40 includes a foot portion 50 slidably positioned along the respective member of frame 20. Foot portion 50 includes first and second arms 51, 55 defining a receptacle therebetween. Arm 51 includes a recessed undercut portion 53 shaped to receive an undercut portion 34 of frame 20 to mount foot portion 50 thereto. The interface between foot portion 50 and undercut portion 34 prevents clamping device 40 from pivoting or lifting from frame 20. Foot portion 50 is positionable on the corresponding member 21, 23, 25, 27 by placing foot portion 50 on frame 20 at the corresponding recess 22, 24, 26, 28. Foot portion 50, and thus clamping device 40, can be slid along the corresponding frame member 21, 23, 25, 27 to the desired location therealong where the receptacle between arms 51, 55 is located along the corresponding undercut portion 34.

Figure 16:
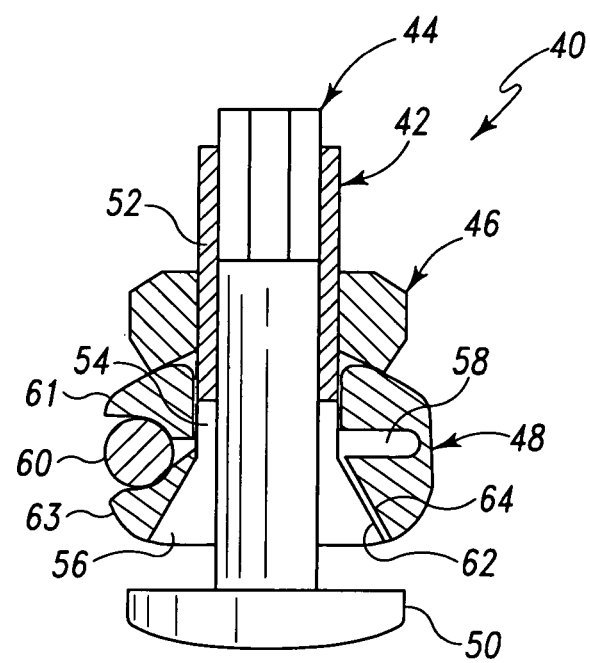
FIG. 16 is a section view of a clamping device comprising a portion of the surgical instrumentation system.

In FIG. 16 clamping device 40 includes a mounting post 44 extending from foot portion 50, and an inner clamping sleeve 42 positioned about mounting post 44. Clamping sleeve 42 includes an upper threaded attachment portion 52 and a lower clamping portion 54. Lower clamping portion 54 includes a frusto-conically shaped lower support member 56 extending thereabout, and at least one slot extending axially through support member 56 to divide clamping portion 54 into a corresponding number of fingers. Accordingly, the fingers of clamping portion 54 can be compressed about mounting post 44 to selectively grip and release mounting post 44 therebetween. Accordingly, clamping sleeve 42 can be axially translated relative to mounting post 44 and clamped at any one of a number of positions therealong to provide elevational adjustment of the respective retractor 120, 220 or distractor mechanism 320 engaged thereto.

A coupler 48 is positionable about clamping sleeve 42, and is supported on a contact surface 62 of lower support member 56. Coupler 48 includes a relief slot 58 formed therein that divides coupler 48 into upper and lower clamping halves 61, 63 joined by an integral hinge. An enlarged receptacle 60 is provided along one side of coupling member 48 in communication with relief slot 58 that is sized to receive shaft assembly 74 of adjustment mechanism 70 therethrough. A clamping nut 46 is threadingly engaged to attachment portion 52, and movable therealong to contact coupling member 48. As clamping nut 46 is threaded downwardly, it contacts coupler 48 to flex clamping halves 61, 63 toward one another, gripping shaft assembly 74 therebetween in receptacle 60. In addition, coupler 48 includes lower contact surface 64 that presses on contact surface 62 to compress clamping portion 54 of clamping sleeve 42 to mounting post 44. Receptacle 60 can be configured to capture shaft assembly 74 therein to prevent shaft assembly 74 from slipping laterally therefrom.

Accordingly, clamping device 40 allows adjustment mechanism 70 and the retractor 120, 220 or distractor mechanism 320 to be repositioned relative to frame 20. When clamping nut 46 is loosened, retractors 120, 220 can be disengaged from adjustment mechanism 70 and pivoted, moved toward the center of frame 20, and/or moved away from the center of frame 20. Clamping nut 46 can then be re-engaged to secure the re-positioned shaft assembly 74 in receptacle 60. Coupler 48 and clamping sleeve 42 can further be repositioned or translated up and down along the length of mounting post 44 to accommodate re-positioning of retractors 120, 220 and distractor mechanisms 320 in the patient.

Other means for securing retractors 120, 220 to frame 20 are also contemplated. Other examples are provided in U.S. Pat. No. 6,083,154, which is incorporated herein by reference in its entirety. With regard to distractor mechanisms 320, the arrangement between the distractor mechanism and anchor, adjustment mechanism, and clamping device can provide a suitably rigid coupling arrangement to maintain distraction of the adjacent vertebrae when distraction devices are removed from the disc space.

One technique for using surgical instrumentation system 10 includes the surgeon making an incision in the skin of the patient to provide access to the facet joints of adjacent vertebrae in a posterior lateral approach. Retractor 120 can be placed in the incision to assist in exposing and identifying the underlying bony structure. Frame 20 can then be placed around retractor 120, and retractor 220 if employed. Adjustment mechanisms 70 extending from retractors 120, 220 can be engaged to clamping devices 40 to maintain and provide for adjustment of the retracted condition of the skin and tissue.

Anchors 100 are engaged to adjacent vertebrae, and anchor extensions 142 are coupled to corresponding ones of the anchors 100 as discussed above. Anchors 100 are engaged to bony structure of the vertebrae positioned on each side of the target disc space. For example, anchors 100 can be engaged in the pedicles of the adjacent vertebrae. The multi-axial heads on anchors 100 allow anchor extensions 142 to be oriented relative to anchors 100 for attachment to the respective portions of frame 20. If employed, retractor portions 332 are then engaged to anchors 100 by sliding retractor portions 332 along the respective anchor extension 142, and engaging retractor portions 332 to the anchor extensions 142 with coupling members 160.

With frame 20 positioned around retractors 120, 220 and distractor mechanisms 320 engaged to anchors 100, the disc space can be distracted with appropriate distraction or spreading instruments. When anchors 100 include multi-axial capabilities, distractor mechanisms 320 can be pivoted relative to the vertebra to which it is mounted. Adjustment mechanisms 70 extending from distractor mechanisms 320 can then be secured to frame 20 with clamping devices 40 when suitably positioned and oriented in the incision. Adjustment mechanisms 70 are then engaged to the respective clamping devices 40 to maintain the distracted disc space condition and retracted tissue condition. Retractors 120, 220 and distractor mechanisms 320 can be adjusted in the desired angular and elevational orientation by means of the adjustment mechanisms 70 and clamping devices 40. The positioning of retractors 120, 220 and distractor mechanisms 320 may be facilitated by the use of push members, handles or the like.

With the access opening formed to the disc space and the disc space distraction properly maintained with surgical instrumentation system 10, surgical procedures can be performed through the minimally invasive access opening provided between distractor mechanisms 320 and the one or more retractors 120, 220. With distractor mechanisms 320 maintaining the distracted disc space, distraction instruments in the disc space can be eliminated during the procedure and enabling a less invasive approach to accommodate the surgical instruments. Examples of instrumentation, techniques and implants suitable for a posterior-lateral approach are provided in PCT Publication No. WO 01/28469 A2 and PCT Application No PCT/US02/15374, each of which is incorporated herein by reference in its entirety. Furthermore, the angulation of the distractor mechanisms with the vertebrae allows the spacing of anchors 100 at the operative site to be as close together as possible, while providing sufficient retraction of tissue in the approach to the operative site to accommodate the surgical instruments.

The retractors 120, 220 and distractor mechanisms 320 can be made of a material which permits effecting a radiographic monitoring during the operation, i.e. a material which is radio-transparent or radio-translucid. It is also contemplated that this material be selected, for example, from the following group: aluminum, titanium, stainless steel, carbon composites, and plastics.

While the invention has been illustrated and described in detail in the drawings and foregoing description, the same is to be considered as illustrative and not restrictive in character. All changes, modifications and equivalents that come within the spirit of the invention as defined by the following claims are desired to be protected.

What is claimed is:

1. A surgical instrumentation system to provide a surgical approach to a patient's spine, comprising:
a frame including multiple portions lying in at least one plane; wherein said frame includes a first portion lying in a first plane and a second portion lying in a second plane that is transversely oriented to the first plane; and
a plurality of retractors attachable to said frame portions, each of said retractors including a blade portion extending transversely to said at least one plane when attached thereto, said blade portion including a tissue contacting surface adapted to contact and retract tissue from the surgical approach; wherein one or more of said retractors is attachable to said first portion and one or more of said retractors is attachable to said second portion; and
at least one adjustment mechanism engageable with at least one of said retractors, wherein said at least one adjustment mechanism includes a shaft within a securement device pivotally coupled with said at least one of said retractors at a pivoting coupling location adjacent a proximal end of said at least one of said retractors, said pivoting coupling location toward said frame portions and said securement device movable along said frame portions, the securement clamping device operable to engage said adjustment mechanism to said frame portions;
wherein said adjustment mechanisms each include: an adjustment handle; a shaft assembly extending from said adjustment handle and including said shaft and an engagement member at an end of said shaft assembly opposite said adjustment handle;
wherein said shaft assembly includes an outer shaft and an inner shaft movably positioned within said outer shaft, said engagement member extending from a distal end of said inner shaft;
wherein said adjustment mechanism includes a pair of plates at a distal end thereof, and each of said retractor includes a pair of proximal flanges pivotally coupled to said pair of plates.

2. The system of claim 1, wherein said adjustment mechanisms each including a first condition in locking engagement with said respective frame portion to fixedly secure said adjustment mechanism relative to said frame portions, said adjustment mechanisms further each including a second condition in which at least one of said retractor is in pivotal engagement with said respective adjustment distractor mechanism to permit said retractor to pivot relative to said frame.

3. The system of claim 2, further comprising clamping devices mounted to said frame portions and releasably engageable to respective ones of said adjustment mechanisms.

4. The system of claim 1, wherein said engagement member includes a number of teeth configured to selectively interdigitate and lockingly engage a number of teeth provided adjacent a proximal end of said retractor, said number of teeth engaging one another along concave-convex pivot path of said retractor.

5. The system of claim 1, wherein said adjustment handle is linked with said inner shaft, said adjustment handle being rotatable to non-rotatably and linearly advance said inner shaft and said engagement member between said first condition and said second condition.

6. The system of claim 1, wherein: each flange of said pair of proximal flanges includes an arcuate slot defining a pivot path of the respective said retractor;
said engagement member includes a slot extending along a longitudinal axis of said shaft assembly; and said adjustment mechanism further comprises a roller pin coupled between said pair of plates and extending through said slot of said engagement member and said arcuate slots of said pair of flanges of said retractor.

7. The system of claim 1, wherein at least one of said retractors include a first side defining a tissue contacting surface and an opposite second side configured to accommodate and support surgical instruments positioned therealong.

8. The system of claim 1, wherein at least one said retractors include a blade portion defining a substantially flat tissue contacting surface extending along a longitudinal axis of said blade portion, and at least another of said retractors include a blade portion defining a concave tissue contacting surface extending along a longitudinal axis of said at least another retractor.

9. The system of claim 1, wherein in an operative position said frame includes a medial portion adapted to lie along the posterior side of the spine, a caudal portion proximate one end of the medial portion and a cephalad portion proximate a second end of the medial portion.

10. The system of claim 9, wherein in said operative position at least one of said plurality of retractors is attachable to said medial portion and is positionable adjacent the spinal mid-line, least one of said plurality of retractors is attachable to said caudal portion and is positionable in a caudal orientation relative to the spine, and least one of said plurality of retractors is attachable to said cephalad portion and is positionable in a cephalad orientation relative to the spine.

11. The system of claim 1, further comprising one or more brackets coupled to at least one frame portion configured to attach to a surgical table securing arm to support the system.

12. A surgical instrumentation system to provide a surgical approach to a patient's spine, comprising:
a frame including multiple portions lying in at least one plane;
a plurality of retractors attachable to said frame portions, each of said retractors including a blade portion extending transversely to said at least one plane, said blade portion including a tissue contacting surface adapted to contact and retract tissue from the surgical approach; and
at least one adjustment mechanism coupled to respective ones of said plurality of retractors, said adjustment mechanisms each including a first condition in locking engagement with said respective adjustment mechanism to fixedly secure said adjustment mechanism relative to one of said frame portions, said adjustment mechanisms further each including a second condition in pivotal engagement with said respective retractor to permit said retractor to pivot relative to said frame portion, wherein said adjustment mechanisms each include: an adjustment handle; a shaft assembly extending from said adjustment handle and an engagement member at a distal end thereof opposite said adjustment handle, said engagement member including a number of teeth configured to selectively interdigitate and lockingly engage a number of teeth provided adjacent a proximal end of said distractor mechanism, said number of teeth engaging one another along concave-convex pivot path of said retractor;

wherein said shaft assembly includes an outer shaft and an inner shaft movably positioned within said outer shaft, said engagement member extending from a distal end of said inner shaft; and a pair of plates at said distal end of said adjustment mechanism and said retractor includes a pair of proximal flanges pivotally coupled to said pair of plates.

13. The system of claim 12, wherein:

each flange of said pair of proximal flanges includes an arcuate slot defining a pivot path of the respective said retractor;

said engagement member includes a slot extending along a longitudinal axis; and said adjustment mechanism further comprises a roller pin coupled between said pair of plates and extending through said slot of said engagement member and said arcuate slots of said pair of flanges of said retractor.

14. The system of claim 12, further comprising another of said plurality of retractors attachable to said frame portion generally opposite said retractor.

15. The system of claim 12, wherein at least one of said retractors include a blade portion defining a substantially flat tissue contacting surface extending along a longitudinal axis of said blade portion, and at least another of said retractors includes a blade portion defining a concave tissue contacting surface extending along a longitudinal axis of said at least another retractor.

16. The system of claim 15, wherein said frame includes at least a first portion and a second portion.

17. The system of claim 16, wherein at least one of said retractors is attachable to said first portion and at least another of said retractors is attachable to said second portion.

18. The system of claim 17, wherein more than one of said retractors are attachable to said first portion of said frame.

19. The system of claim 17, wherein said frame further comprises a third portion extending between said first and second portions, said at least one of said plurality of retractors is attachable to said third portion.

20. The system of claim 12, wherein in an operative position said frame includes a medial portion adapted to lie along the posterior side of the spine, a caudal portion proximate one end of the medial portion and a cephalad portion proximate a second end of the medial portion.

21. The system of claim 20, wherein in said operative position at least one of said plurality of retractors is attachable to said medial portion and is positionable adjacent the spinal mid-line, least one of said plurality of retractors is attachable to said caudal portion and is positionable in a caudal orientation relative to the spine, and least one of said plurality of retractors is attachable to said cephalad portion and is positionable in a cephalad orientation relative to the spine.

22. The system of claim 12, further comprising one or more brackets coupled to at least one frame portion configured to attach to a surgical table securing arm to support the system.

23. A surgical instrumentation system to provide a surgical approach to a patient's spine, comprising:

a frame including a first portion and a second portion;

a plurality of retractors secured to the frame and adapted to pivot relative to the frame, at least one of said retractors being secured to said first portion of said frame and extending transversely to said first portion and at least one other of said retractors being secured to said second portion of said frame and extending transversely to said second portion;

an adjustment mechanism for facilitating pivotal adjustment of the retractors, said adjustment mechanism includes: an adjustment handle; a shaft assembly extending from said adjustment handle and including said shaft and an engagement member at an end of said shaft assembly opposite said adjustment handle;

wherein said shaft assembly includes an outer shaft and an inner shaft movably positioned within said outer shaft, said engagement member extending from a distal end of said inner shaft;

wherein said adjustment mechanism includes a pair of plates at a distal end thereof, and each of said retractor includes a pair of proximal flanges pivotally coupled to said pair of plates;

wherein said retractors are secured to the frame with securement devices each including a receptacle being slideable along a respective one of said first and second portions of said frame; and wherein each of said retractors is lockable in a selectable pivoting location by engagement of the adjustment mechanism with a portion of the retractor.

24. The system of claim 23, wherein said frame further comprises a third portion, at least one of said retractors being secured to said third portion of said frame and extending transversely to said third portion.

25. The system of claim 23, wherein at least one of said plurality of retractors include a blade portion defining a substantially flat tissue contacting surface extending along a longitudinal axis of said blade portion, and at least another of said plurality of retractors includes a blade portion defining a concave tissue contacting surface extending along a longitudinal axis of said at least another retractor.

26. The system of claim 23, wherein at least one of said plurality of retractors include a first side defining a tissue contacting surface and an opposite second side configured to accommodate and support surgical instruments positioned therealong.

27. The system of claim 23, wherein at least one of said plurality of retractors include a tissue contacting surface adapted to contact and retract tissue from the surgical approach.

28. The system of claim 23, further comprising one or more brackets coupled to at least one frame portion configured to attach to a surgical table securing arm to support the system.

* * * * *